United States Patent [19]

Carlemalm

[11] 4,368,312
[45] Jan. 11, 1983

[54] EMBEDDING MEDIUM SUITABLE FOR THE PREPARATION OF THIN SECTIONS OF EMBEDDED BIOLOGICAL MATERIALS

[75] Inventor: Eric Carlemalm, Therwil, Switzerland

[73] Assignee: Chemische Werke Lowi G.m.b.H., Waldkraiburg, Fed. Rep. of Germany

[21] Appl. No.: 242,025

[22] Filed: Mar. 9, 1981

[51] Int. Cl.$^3$ .......................................... C08F 120/10
[52] U.S. Cl. .................................................. 526/323.2
[58] Field of Search ............................. 526/323.2, 320

[56] References Cited

U.S. PATENT DOCUMENTS 3,503,942 10/1965 Leiderman et al. .................. 526/320
3,983,083 9/1976 Kaetsu et al. ......................... 526/320

FOREIGN PATENT DOCUMENTS 55-104311 8/1980 Japan .................................... 526/320

OTHER PUBLICATIONS

Newman et al., U.S. Dept. of Commerce, Research Paper RP 2020, vol. 43, Sep. 1949.
Rosenberg et al., Journal of Ultrastructure Research 19, 196–199, 1967.
Ledue et al., Journal of Cell Biology, vol. 26, 137–155, 1965.
McLean et al., Journal of Cell Biology, 20, 518–521, 1964.

Primary Examiner—William F. Hamrock
Assistant Examiner—Peter F. Kulkosky
Attorney, Agent, or Firm—Oblon, Fisher, Spivak, McClelland & Maier

[57] ABSTRACT

The invention concerns embedding media for producing essentially non-polar and polar embedding mediums. The non-polar embedding medium comprises ethylmethacrylate, n-hexylmethacrylate, triethyleneglycoldimethacrylate and a small amount of polymerization initiator. The polar embedding medium comprises 2-hydroxyethylacrylate, 2-hydroxypropylmethacrylate, n-hexylmethacrylate, triethyleneglycoldimethacrylate, and a small amount of polymerization initiator. The embedding mediums of the invention are particularly suitable for the preparation of a polymer embedded biological material for light or electron microscopic study of thin sections thereof. The embedding mediums can be polymerized at low temperature and UV light employed for initiating polymerization.

4 Claims, No Drawings

EMBEDDING MEDIUM SUITABLE FOR THE PREPARATION OF THIN SECTIONS OF EMBEDDED BIOLOGICAL MATERIALS

This invention relates to embedding mediums for the preparation of thin sections of embedded biological materials. The thin sections are of the type which may be employed for light or electron microscopic study of the embedded biological materials.

The preparation of biological specimens by the embedding thin sectioning technique, although usually adequate for general cytological work, has severe limitations for high resolution electron microscopy as in the molecular region. In order to improve the amount of useful information retrievable, a number of deleterious effects must be minimised, including the effects of molecular denaturation, supramolecular disordering, damage by sectioning, and other factors related to observation, such as staining, and beam damage due to irradiation in the electron microscope.

Most attempts to improve embedding techniques in the past have involved the consideration that a water-soluble resin renders dehydration essentially unnecessary and that use of such resins will not lead to solvent-induced denaturation. What does not appear to have been properly observed or considered is that the liquid resin itself can be a solvent which leads to solvent denaturation. Furthermore, the fact that a liquid resin may be water-soluble does not ensure that the initial polar environment of cell structures would be maintained.

All procedures of the past for the preparation of thin sections of embedded biological materials are characterised by the inability to independently alter several parameters, including particularly:
the effect on biological materials such as proteins and lipoproteins when water is replaced by organic fluids employed in the embedding procedure
the effect of polarity of the organic solvent and embedding medium,
effects of temperature,
effects of water content remaining after dehydration,
effects of the type and duration of fixation,
effect of the nature of heavy metal staining.

It is an object of the present invention to provide new embedding mediums enabling parameters such as above to be varied independently. This enables determination of the influence of each parameter on the different structural aspects in biological materials such as protenaceous complexes and protein-rich lipoprotein membranes. The parameters are extremely interdependent or intercorrelated, as for example illustrated by the fact that aminoacid residues at the surface of proteins as well as polar heads of lipids are firmly associated with a layer of water, the hydration shell, and the fact that the binding of this water on proteins is different for different molecular surfaces and can become "melted away" at different temperatures. Thus, the higher this "melting temperature", the "firmer" is the water bound. This phenomenon is involved in the formation of the hydrophobic bond, which becomes established only upon raising of temperature. Such bonds are entropy driven, i.e. the disorder associated with "melting" of the hydration water increases the entropy more than the association (ordering) of proteins does decrease it. Many believe that the hydration shell is an important factor in establishing the tertiary structure of a protein. Pertubing or removing it, would lead to the conformational changes associated with denaturation. Therefore, the fate of the hydration shell during embedding must be considered. Similarly, with highly polar organic solvents or embedding mediums, in which water is soluble, the possibility of competitive effects between these liquids and the biological material for the remaining water of hydration must be considered. Particularly in a polar resin, a sort of competition might occur which removes the hydration shell, if water has a higher affinity to the resin. Since no experimental data are available as yet, this question has to be solved empirically for the embedding. Non-polar solvents or embedding mediums on the contrary have no affinity for water and it can be envisaged that the hydration shell is not removed, provided obviously that it was maintained during dehydration. This returns the considerations related to polar solvents.

In accordance with the invention, there are provided non-polar and polar embedding medium components for admixture with a cross-linking agent and a small amount of polymerisation initiator. A variety of components may be suitable for preparing non-polar and polar embedding mediums and similarly a variety of cross-linking agents may be suitable.

In the case of the polymerisation initiator, practically any substance capable of providing a free radical with sufficient reactivity for free radical polymerisation would be suitable for use in preparing embedding mediums of the present invention. At the same time, the nature of the polymerisation initiator and the amount employed in the preparation of the embedding medium would in general be chosen so that polymerisation is not too rapid which can cause perturbation of the cellular structures such as by "polymerisation explosion" or so that no significant amount of heat is generated, which can also lead to perturbation or distortion of cellular structures. Any benzoin would in essence be suitable for use as the polymerisation initiator, benzoin monomethylether being exemplary. The amount of polymerisation initiator employed in preparing the embedding mediums of the present invention is not critical, but would be at least 0.1% by weight based on the total weight of the embedding medium prepared. More than 1% of polymerisation initiator would not provide any benefit.

The cross-linking agent should be present in a sufficient amount in each of the embedding mediums of the present invention since it is probable that the gelling effect of the cross-linking agent on the medium will lower or exclude monomer flow from one region to another in embedded cellular structures which can result in "polymerisation explosion" of the nature mentioned above, or rupture of sensitive membranes defining cell structures.

With the same considerations as above related to polymerisation rate in mind, the energy for polymerisation initiator, for example UV irradiation, should be such that polymerisation is not too rapid.

Discussing now first the non-polar embedding medium of the present invention, two non-polar monomers for admixture, or already admixed, have been established to be suitable. These are ethylmethacrylate and n-hexylmethacrylate, although it is to be understood that other non-polar monomers could be employed without departing from the essential characteristics of the present invention. In view of the very extensive experimentation necessary to establish suitable ratios, effects of specific cross-linking agents on other non-polar monomers, the non-polar embedding medium of the present invention will only be described and claimed in relation to ethylmethacrylate and n-hexylmethacrylate monomers. Similarly, in the case of the cross-linking agent, only triethyleneglycoldimethacrylate will be described and claimed as a cross-linking agent actually known and established to be suitable for this purpose at the ratios indicated.

In the case of the polar embedding medium of the present invention, two polar monomers for admixture, or already admixed, have been established to be suitable. These are 2-hydroxyethylacrylate and 2-hydroxypropylmethacrylate. These two polar monomers are also admixed with an amount of a non-polar monomer, which for similar reasons as discussed above is identified as n-hexylmethacrylate. Triethyleneglycoldimethacrylate is employed as cross-linking agent in the preparation of the polar embedding medium.

As already indicated, the ratios of the components employed in the preparation of the embedding mediums needs to be established, and upper and lower limits determined outside of which unsatisfactory results would be obtained.

The following Table I shows the components and parts by weight which are employed for the preparation of a non-polar embedding medium:

TABLE I

| component | parts by weight | typical parts by weight |
| --- | --- | --- |
| ethylmethacrylate | 4 to 4.9 | 4.45 |
| n-hexylmethacrylate | 0.9 to 1.2 | 1.08 |
| triethyleneglycoldimethacrylate | 0.65 to 1.3 | 0.969 |
| polymerisation initiator* | 0.0065 to 0.65 | 0.0325 |

*benzoin monomethylether

The following Table II shows the components and parts by weight which are employed for the preparation of a polar embedding medium:

TABLE II

| component | parts by weight | typical parts by weight |
| --- | --- | --- |
| 2-hydroxyethylacrylate | 1.4 to 1.74 | 1.6 |
| 2-hydroxypropylmethacrylate | 2.9 to 3.55 | 3.22 |
| n-hexylmethacrylate | 0.74 to 0.9 | 0.82 |
| triethyleneglycoldimethacrylate | 0.6 to 1.25 | 0.88 |
| polymerisation initiator* | 0.0065 to 0.065 | 0.0325 |

*benzoin monomethylether

As will be recognised from Table I above, the ratio by weight of ethylmethacrylate:n-hexylmethacrylate can lie between the two extreme limits of 4:1.2 and 4.9:0.9. This is equivalent to a ratio of ethylmethacrylate:n-hexylmethacrylate of 3.3 to 5.4:1. Similarly, the ratio by weight of the combined ethylmethacrylate and n-hexylmethacrylate:triethyleneglycoldimethacrylate can lie between the two extreme limits of 4+0.9:1.3 and 4.9+1.2:0.65. This is equivalent to a ratio of the combined ethylmethacrylate and n-hexylmethacrylate:-triethyleneglycoldimethacrylate of 3.77 to 9.38:1. The amount of polymerisation initiator shown in the Table I corresponds to 0.1 to 1% of the total weight of the embedding medium.

Most conveniently, the ethylmethacrylate and n-hexylmethacrylate are provided in combined form in a single container at said ratio of 3.3 to 5.4:1 and the triethyleneglycoldimethacrylate cross-linking agent is provided in a separate container. In preparing a non-polar embedding medium 3.77 to 9.38 parts by weight of the combined ethylmethacrylate and n-hexylmethacrylate are then admixed with the triethyleneglycoldimethacrylate and the small amount of polymerisation initiator which is conveniently provided in a further separate container. A three component package for preparing the non-polar embedding medium is therefore a convenient means for making available the non-polar embedding medium components.

In the same fashion as above, and turning now to Table II concerning the polar embedding medium, it will be recognised that the ratio by weight of the 2-hydroxyethylacrylate:2-hydroxypropylmethacrylate can lie between the two extreme limits of 1.4:3.5 and 1.74:2.9. This is equivalent to a ratio of 2-hydroxyethylacrylate:2-hydroxypropylmethacrylate of 0.39 to 0.60:1. Similarly, the ratio by weight of the combined 2-hydroxyethylacrylate and 2-hydroxypropylmethacrylate:n-hexylmethacrylate can lie between the two extreme limits of 1.4+2.9:0.9 and 1.74+3.55:0.74. This is equivalent to a ratio by weight of the combined 2-hydroxyethylacrylate and 2-hydroxypropylmethacrylate:n-hexylmethacrylate of 4.78 to 7.15:1. The ratio by weight of the combined 2-hydroxyethylacrylate, 2-hydroxypropylmethacrylate and n-hexylmethacrylate:triethyleneglycoldimethacrylate can lie between the extreme limits of 1.4+2.9+0.74:1.25 and 1.74+3.55+0.9:0.6, which is equivalent to a ratio by weight of combined 2-hydroxyethylacrylate, 2-hydroxypropylmethacrylate and n-hexylmethacrylate:triethyleneglycoldimethacrylate of 3.77 to 9.38:1.

The 2-hydroxyethylacrylate and 2-hydroxypropylmethacrylate may be provided in combined form in a single container at said ratio of 0.39 to 0.60:1. In this case, the n-hexylmethacrylate and triethyleneglycoldimethacrylate are provided in separate containers. Alternatively, the 2-hydroxyethylacrylate and n-hexylmethacrylate are provided in combined admixed form in a single container at a ratio by weight of between 1.4:0.9 and 1.74:0.74, which is equivalent to a ratio by weight of 2-hydroxyethylacrylate:n-hexylmethacrylate of 1.56 to 2.35:1. The 2-hydroxypropylmethacrylate and triethyleneglycoldimethacrylate are then provided in separate containers. Yet a further alternative is to provide the 2-hydroxypropylmethacrylate and the n-hexylmethacrylate in combined admixed form in a single container at a ratio by weight of between 2.9:0.9 and 3.55:0.74, which is equivalent to a ratio by weight of 2-hydroxypropylmethacrylate:n-hexylmethacrylate of 3.22 to 4.80:1. In this further alternative, the 2-hydroxyethylacrylate and the triethyleneglycoldimethacrylate are provided in separate containers. Most conveniently, the 2-hydroxyethylacrylate, 2-hydroxypropylmethacrylate and n-hexylmethacrylate are provided in combined admixed form in a single container at a ratio by weight of 2-hydroxyethylacrylate:2-hydroxypropylmethacrylate:n-hexylmethacrylate of 1.4 to 1.74:2.9 to 3.55:0.74 to 0.9 as reflected in the Table II above. Where the 2-hydroxyethylacrylate and 2-hydroxypropylmethacrylate are provided in combined admixed form, 0.39 to 0.60 parts by weight of this combined form would be admixed with 1 part by weight of 2-hydroxypropylmethacrylate and then 4.03 to 10.32 parts by weight of the resulting mixture would be admixed with 1 part by weight of the triethyleneglycoldimethacrylate and the polymerisation initiator added.

Where the 2-hydroxyethylacrylate and n-hexylmethacrylate are provided in combined admixed form in a single container, 0.60 to 0.91 parts by weight of this combined form are admixed with 1 part by weight of 2-hydroxypropylmethacrylate. As before, 4.03 to 10.32 parts by weight of the resulting mixture would be admixed with 1 part by weight of the triethyleneglycoldimethacrylate and the polymerisation initiator added.

In the case where 2-hydroxypropylmethacrylate and n-hexylmethacrylate are provided in combined admixed form in a single container, 2.09 to 3.12 parts by weight of this combined form would be admixed with 1 part by weight of 2-hydroxyethylacrylate. Again, 4.03 to 10.32 parts by weight of the resulting mixture would be admixed with 1 part by weight of the triethyleneglycoldimethacrylate and the polymerisation initiator added.

As already indicated, the 2-hydroxyethylacrylate, 2-hydroxypropylmethacrylate and the n-hexylmethacrylate are most conveniently provided in admixed form in a single container. In this case, 4.03 to 10.32 parts by weight of the admixed form are simply admixed with 1 part by weight of the triethyleneglycoldimethacrylate and the polymerisation initiator added.

Depending on the ratios chosen within the limits indicated above, the hardness and hence adaptability to sectioning can be adjusted. Thus, for example, in the non-polar embedding medium of the present invention higher proportions of ethylmethacrylate (within the limits indicated) inclines the embedding medium composition to produce an embedding having harder properties, whereas higher proportions of n-hexylmethacrylate (within the limits indicated) inclines the embedding medium composition to produce an embedding having softer properties. A balance between the two properties can be achieved as desired by chosing the ratios of admixture. Similarly, if too much cross-linking agent, i.e. triethyleneglycoldimethacrylate is employed, the resulting embedding medium will form an embedding which would be too brittle for sectioning.

The embedding mediums of the present invention are particularly characterised by a relatively high proportion of cross-linking agent which is higher than any previous embedding mediums employed in microscopy. The embedding mediums of the invention are capable of polymerisation at low temperatures down to −50° C. A further characteristic of the embedding mediums of the present invention is their capability to absorb ultraviolet light of a wavelength which does not act on embedded biological materials such as proteins, nucleic acids and hemoglobin. It will be appreciated that if energy sources are employed which involve wavelength emissions which are absorbed by the embedded materials, the energy would not be available for activation of the polymerisation initiator. Also, it will be appreciated that one would not wish transmitted energy to act on the biological materials since this might act to destroy cellular structures.

As indicated above, a variety of components may be suitable for preparing non-polar and polar embedding mediums. Further exemplary monofunctional monomers which could be suitable for preparing embedding mediums having properties equivalent to those of the invention are 2-hydroxyethylmethacrylate, 2-hydroxypropylacrylate, propylmethacrylate and acrylic and methacrylic esters of benzyl alcohol. Other crosslinking agents which could prove suitable include ethyleneglycoldimethacrylate and hexandioldimethacrylate.

Exemplary polymerisation initiators suitable for low temperature UV light polymerisation and which possess the necessary activity are benzoin, benzoinethylether, benzoin monomethylether, 2,2-dimethoxy-2-phenylacetophenone and 2-hydroxy2-methyl-1-phenyl-propan-1-one.

The following preparation schemes shown in Tables III and IV below are examples of two embedding procedures employing the embedding media of the present invention which have provided entirely satisfactory results at low temperatures.

TABLE III

| polar embedding medium | | | |
|---|---|---|---|
| 1. | Desired aldehyde fixation at 0° C.−20° C. | | |
| 2. | 65% ethyleneglycol | 60 min | 0° C. |
| 3. | 80% ethanol | 120 min | −50° C. |
| 4. | 100% polar medium typical of Table II diluted 1:1 with 80% ethanol | 60 min | −50° C. |
| 5. | 100% polar medium diluted 2:1 with 80% ethanol | 60 min | −40° C. |
| 6. | 100% polar medium | 60 min | −35° C. |
| 7. | 100% polar medium | overnight or longer | −35° C. |

TABLE IV

| nonpolar embedding medium | | | |
|---|---|---|---|
| 1. | Desired aldehyde fixation at 0° C.−20° C. | | |
| 2. | 65% ethyleneglycol | 60 min | 0° C. |
| 3. | 70% ethanol | 60 min | −50° C. |
| 4. | 90% ethanol | 120 min | −70° C. |
| 5. | 100% non-polar medium typical of Table I diluted 1:1 with 90% ethanol | 60 min | −70° C. |
| 6. | 100% non-polar medium diluted 2:1 with 90% ethanol | 60 min | −70° C. |
| 7. | 100% non-polar medium | 60 min | −70° C. |
| 8. | 100% non-polar medium | overnight or longer | |

(The schemes can be adapted for any other temperature or non-polar or polar solvent as long as solubility allows it).

Polymerisation:

Both resins are polymerised by indirect UV-irradiation 360 mm (2×Philips TLAD 15W/05 or equivalent) at −50° C. to −40° C. at a distance of 30-40 cm, over 24 hours. Sectioning quality improves when the blocks are further hardened at room temperature for 2-3 days. Polymerisation can also be carried out at room temperature.

Sectioning and Staining

The embedding mediums, easily yield silver to grey sections on diamond or glass knives. Optical sectioning requires a moderate cutting speed. Poststaining is easily effected with uranyl acetate; Reynold's lead citrate appears acceptable for low magnification work. The polar embedding medium provides excellent results with immunostaining on sections with the known protein A-gold complex technique.

To exemplify the use of the polar and non-polar embedding mediums and their properties, two crystalline protein preparations were employed which could reasonably model the behaviour of general biological systems during embedding. The first protein is aspartate aminotransferase (AAT), a relatively stable protein which produces a crystal that is resistant to molecular disordering. Such a crystal would allow the denaturation of the protein to be monitored. The second protein is catalase (CAT), a well-known test specimen for electron microscopy. The type of (CAT) crystals used in this study are very susceptible to disordering when the solvent is altered in character; a molecular disordering which most likely occurs during the preparation of any biological material. With such protein crystals, the effects of fixation, dehydration, and resin curing can be observed through X-ray diffraction. The working temperatures range from −35° C. to −70° C., depending on the resin. As an added advantage, the mechanical properties (for sectioning) and chemical characteristics (i.e. hydrophilicity) can be easily varied.

Procedure

Both crystals were fixed using 0.5% glutaraldehyde in their respective mother liquors for 12–16 hours at 4° C. These fixed crystals were then washed in 0.4 M K+PO4 (for CAT) or 0.4 M Na+ citrate (for AAT); both buffers adjusted to pH 7.4. Osmium fixation was performed in either citrate or phosphate buffer on an ice bath. From this point onwards, the embedding study split into two different procedures: conventional embedding systems and low-temperature systems.

In the conventional series, the crystals were dehydrated using a stepwise procedure of 50%, 70%, 90%, 100% dehydrating agent/water mixtures. One of the following dehydrating agents were employed in each test: dimethyl formamide, ethanol, ethylene glycol. All dehydration steps were carried out either at 0° C. or 20° C. For infiltration three steps were used: 1 to 2, Epon 812/dehydrating agent; 2:1, Epon 812/dehydrating agent; and finally 100% Epon 812. In all cases, typical dehydration and infiltration times were used. For crystal preparations which were to be hardened, the Epon 812 was polymerised at 45° C. for 12 h, then at 70° C. for 4 days.

The low temperature procedures involved only three dehydration agents: ethylene glycol, ethanol and methanol. The dehydration was carried out as follows: 50% dehydrating agent in H2O at 0° C., then 80–90% dehydrating agent/H2O at −50° C. For infiltration the crystals were treated with one part resin to one part 80–90% dehydrating agent in H2O, then placed into 100% resin. The length of time for each step was just long enough to insure adequate exchange. The polar and non-polar embedding mediums were tested. The use of the polar medium limits the minimum temperature to −35° C., so that just before infiltration the temperature was raised. If X-ray analysis was to be done on the un-hardened crystals, the temperature was slowly raised to room temperature. Table V below shows the influence on (AAT) and (CAT) protein crystals of various steps within various embedding media. The embedding media of the present invention are also compared with Epon 812 and HPMA and HEM Leduc embedding mediums known in the art.

TABLE V

|   | Aspartic Amino Transferase | Catalase |
|---|---|---|
| 1. Fixation: | | |
| Glutaraldehyde 0.5% overnight | no influence to 0.28 nm | no influence to 0.3 nm |
| OsO4 1.0% 1 h. | does not diffract | does not diffract |
| OsO4 0.1% FRESH 1 h. | ca. 0.8 nm | ca. 1.2 nm |
| 2. Dehydration: | | |
| Ethanol, methanol 75% DMF and ethyleneglycol 0–20° C. | little influence | ca. 1.5 nm |
| Methanol, DMF 100% and ethyleneglycol 0–20° C. | ca. 1 nm | does not diffract |
| Ethanol 100% 0–20° C. | ca. 1 nm | ca. 3 nm |

|   | Liquid: (nm) | Cured: (nm) | Liquid: (nm) | Cured: (nm) |
|---|---|---|---|---|
| 3. Dehydrated and infiltrated: | | | | |
| Methanol 80–90%, polar medium −35° C. | 0.8–0.9 | 0.8–1.0 | 2.0 | 2.0 |
| Ethyleneglycol 80–90%, polar medium −35° C. | 0.5–0.7 | 0.6–0.7 | 3.0 | 3.0 |
| Ethanol, Epon 812, room-temperature | 1 | 1.0–1.2 | does not | diffract |
| Methanol 90%, non-polar medium −50° C. | — | — | — | 1.2 |
| Ethanol 90%, non-polar medium −50° C. | — | — | 0.8 | 0.8–0.9 |
| HPMA Leduc 0° C. | — | 0.8 | — | — |
| HEM Leduc 0° C. | — | 0.8 | — | — |

Fixation

Glutaraldehyde fixation did not affect the quality of diffraction for either crystal. Some intensity changes were observed. Osmium fixation using "conventional" concentrations destroyed all diffraction. This was probably due to uncontrolled precipitation of the metal. Low OsO4 concentrations (0.001%–0.1%) did maintain some diffraction in the crystal, but the resolution limit decreased with increasing OsO4 concentration.

Dehydration

AAT, when fixed, could easily have all of its water removed and still maintain diffraction out to 1.0 nm while at 0°–20° C. Such is not the case with catalase: all diffraction is lost when it is dehydrated at such temperatures. At low temperature, both AAT and CAT have improved diffraction. AAT prefers ethylene glycol while CAT prefers ethanol.

Resin Step

AAT maintains diffraction out to 0.5 nm in liquid polar medium, and out to 0.6 nm in the hardened resin. In Epon 812, AAT did not diffract better than 1.0 nm. On the other hand, AAT shows high order diffraction only in non-polar medium. In liquid non-polar medium, CAT diffracts to 0.8 nm and does not appreciably lose this diffraction during polymerisation.

In the case of Epon 812, it is impossible to gain the advantages offered by low temperature embedding procedures, which is typical of any epoxy resins which cannot be cured at low temperature. In the case of the Leduc embedding mediums, which do have polar properties, these are partly prepolymerised preparations resulting in too high viscosity which again eliminates possibilities to gain the advantages offered by low temperature embedding procedures.

The polar embedding medium of the present invention is water compatible and provides rapid, but uniform, infiltration and UV-polymerisation without sacrificing sectioning quality. The medium maintains the low viscosity and water-miscible characteristics of previous methacrylate formulations, but does not suffer from the "melting" phenomenon during irradiation in the microscope. The inherent low viscosity of the liquid medium allows for the exploitation of a broad temperature range for specimen preparation, and can easily infiltrate a specimen and be hardened at temperatures as low as −35° C. Thus, an embedding procedure for sensitive structures can be easily designed to take advantage of the stabilizing effects of low temperatures. The polar medium also provides excellent results with immunostaining techniques on sections.

The non-polar embedding medium of the invention is a hydrophobic medium which produces blocks of excellent sectioning quality. The medium retains the properties of low viscosity and uniform polymerisation, but adds the capability of embedding material at very low temperatures. The non-polar medium can be used routinely at temperatures as low as −70° C. At these low temperatures, biological material is stabilized and may even retain its bound water. The medium also provides excellent results also under conventional conditions.

The mediums of the invention should be prepared in brown glass containers or otherwise protected from direct light. All the components are readily miscible with each other. Excessive stirring should be avoided. Methacrylates and acrylates do cause eczema on sensitive persons, so that it is strongly recommended to use gloves when there is risk of skin contact. Polypropylene or polyethylene are suitable but not gloves made from other plastic material.

Typical dehydration and infiltration preparation schemes for embedding media at low temperatures are given in Table VI below:

TABLE VI polar medium

| | | | |
|---|---|---|---|
| 1. | Desired aldehyde fixation at 0° C. to 20° C. | | |
| 2. | 30% ethanol with water | 30 min | 0° C. |
| 3. | 50% ethanol with water | 60 min | −20° C. |
| 4. | 70% ethanol with water | 60 min | −35° C. |
| 5. | 90% ethanol with water | 120 min | −35° C. |
| 6. | 100% polar medium diluted 1:1 with 90% ethanol | 60 min | −35° C. |
| 7. | 100% polar medium diluted 2:1 with 90% ethanol | 60 min | −35° C. |
| 8. | 100% polar medium | 60 min | −35° C. |
| 9. | 100% polar medium | overnight | −35° C. | nonpolar medium

| | | | |
|---|---|---|---|
| 1. | Desired aldehyde fixation at 0° C. to 20° C. | | |
| 2. | 30% ethanol with water | 30 min | 0° C. |
| 3. | 50% ethanol with water | 60 min | −20° C. |
| 4. | 70% ethanol with water | 60 min | −50° C. |
| 5. | 90% ethanol with water | 120 min | −50 to −70° C. |
| 6. | 100% nonpolar medium diluted 1:1 with 90% ethanol | 60 min | −50 to −70° C. |
| 7. | 100% nonpolar medium diluted 2:1 with 90% ethanol | 60 min | −50 to −70° C. |
| 8. | 100% nonpolar medium | 60 min | −50 to −70° C. |
| 9. | 100% nonpolar medium | overnight | −50 to −70° C. |

At all temperatures below 0° C., care must be taken not to allow the residual water in the specimen to freeze during the dehydration steps.

Both resins can be hardened at room temperature with direct irradiation. However, it is recommended that the original initiator es exchanged for the same amount of benzoin ethylether. Room temperature polymerised blocks can be ready for sectioning after a few hours.

General Characteristics

Specimens embedded with the media of the present invention specimens show that excellent ultrastructural preservation is feasible without heavy metal fixation. Enough contrast for observation may be subsequently introduced through section straining or by dark-field microscopy. The polar medium is particularly suitable for non-dark-field observation due to its low density as compared to conventional embedding media.

A further practical application for the embedding media of the present invention is embedding of biological, archeological and other artifacts for preservation purposes.

I claim:

1. A method of producing an essentially nonpolar embedding medium, which consists essentially of the step of admixing ethylmethacrylate, n-hexylmethacrylate, triethyleneglycoldimethacrylate and a free radical polymerisation initiator at a ratio by weight of ethylmethacrylate:n-hexylmethacrylate of 3.3 to 5.4:1, a ratio by weight of the combined ethylmethacrylate and n-hexylmethacrylate:triethyleneglycoldimethacrylate of 3.77 to 9.38:1, and the polymerisation initiator being included in the mixture in a small amount of from about 0.1% to about 1% by weight based on the total weight of the resulting embedding medium, the purity of each of the components being at least 90% by weight.

2. A method according to claim 1, in which the ethylmethacrylate and the n-hexylmethacrylate are provided in combined admixed form at said ratio by weight of 3.3 to 5.4:1 and in which 3.77 to 9.38 parts by weight of this combined form are then admixed with 1 part by weight of triethyleneglycoldimethacrylate and the said small amount of polymerisation initiator.

3. A non-polar embedding medium for the preparation of a biological material embedding composition having the following components at the parts by weight shown in the following table:

| component | parts by weight |
|---|---|
| ethylmethacrylate | 4 to 4.9 |
| n-hexylmethacrylate | 0.9 to 1.2 |
| triethyleneglycoldimethacrylate | 0.65 to 1.3 |
| polymerisation initiator | 0.0065 to 0.65 |

4. A non-polar embedding medium for the preparation of a biological material embedding composition according to claim 3, in which typical parts by weight of said components are as shown in the following table:

| component | parts by weight |
|---|---|
| ethylmetacrylate | 4.45 |
| n-hexylmethacrylate | 1.08 |
| triethyleneglycoldimethacrylate | 0.969 |
| polymerisation initiator | 0.0325 |

* * * * *